US006384046B1

(12) United States Patent
Schuler et al.

(10) Patent No.: US 6,384,046 B1
(45) Date of Patent: May 7, 2002

(54) USE OF 40-O-(2-HYDROXY) ETHYLRAPANYCIN FOR TREATMENT OF RESTENOSIS AND OTHER DISORDERS

(75) Inventors: Walter Schuler, Grenzach-Wyhlen (DE); Hendrik J. Schuurman, Basel; Gisbert Weckbecker, Biel-Benken, both of (CH); Hans-Günter Zerwes, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/712,359

(22) Filed: Nov. 14, 2000

Related U.S. Application Data

(63) Continuation of application No. 09/155,210, filed as application No. PCT/EP97/01548 on Mar. 26, 1997, now abandoned.

(30) Foreign Application Priority Data

Mar. 27, 1996 (GB) .............................................. 9606452

(51) Int. Cl.⁷ .............................................. A61K 31/44
(52) U.S. Cl. ....................................................... 514/291
(58) Field of Search ......................................... 514/291

(56) References Cited

U.S. PATENT DOCUMENTS

| 5,362,718 A | | 11/1994 | Skotnicki et al. .............. 514/63 |
| 5,516,781 A | * | 5/1996 | Morris et al. ................ 514/291 |
| 5,665,772 A | * | 9/1997 | Cottens et al. .............. 514/514 |

FOREIGN PATENT DOCUMENTS

| EP | 551 182 | 7/1993 |
| EP | 568 310 | 11/1993 |
| EP | 691 130 | 1/1996 |
| WO | WO 94/09010 | 4/1994 |
| WO | WO 96/41807 | 12/1996 |

OTHER PUBLICATIONS

Ikonen et al., "Sirolimus (Rapamycin) Halts and Reverses Progression of Allograft Vascular Disease in Non–Human Primates", Transplantation, vol. 70, No. 6, pp. 969–975 (2000).

Matas et al., "Chronic Rejection", J. Am. Soc. Nephrol., vol. 4, Suppl. 1, pp. S23–S29 (1994).

Kahan, "The Potential Role of Rapamycin in Pediatric Transplantation as Observed from Adult Studies", Pediatr Transplantation, vol. 3, pp.175–180 (1999).

Sadrani et al., "Chemical Modification of Rapamycin: The Discovery of SDZ RAD", Transplant. Proc., vol. 30, pp. 2192–2194 (1998).

Fellstrom et al., "Pathogenesis and Treatment Perspectives of Chronic Graft Rejection (CVR)", Immunological Reviews, No. 134, pp. 83–98 (1993).

Meiser et al., "Effects of Cyclosporin, FK506, and Rapamycin on Graft–Vessel Disease", Lancet, vol. 388, pp. 1297–1298 (1991).

Gregory et al., "The Use of New Antiproliferative Immunosuppressants is a Novel and Highly Effective Stategy for the Prevention of Vascular Occulusive Disease", J. Heart Lung Transpl., vol. 11, Pt. 11, p. 197 (1992).

Morris et al., "Immunosuppressive Effects of the Morpholinoethyl Ester of Mycophenolic Acid (RS–61443) in Rat and Nonhuman Primate Recipients of Heart Allografts", Transplant. Proc., vol. 23, No. 2, Suppl. 2, pp. 19–25 (1991).

* cited by examiner

Primary Examiner—William R. A. Jarvis
(74) Attorney, Agent, or Firm—Thomas R. Savitsky; Diane E. Furman

(57) ABSTRACT

This invention relates to the use of 40-O-(2-hydroxy)ethylrapamycin for the prevention or treatment of neointimal proliferation and thickening, restenosis, and vascular occlusion following vascular injury.

4 Claims, No Drawings

USE OF 40-O-(2-HYDROXY) ETHYLRAPANYCIN FOR TREATMENT OF RESTENOSIS AND OTHER DISORDERS

This application is a continuation of Ser. No. 09/155,210, filed Sep. 23, 1998, now abandoned, which is a 371 of PCT/EP97/01548, filed Mar. 26, 1997.

The present invention relates to a new use, in particular a new use for a compound group comprising derivatives of rapamycin, in free form or in pharmaceutically acceptable salt or complex form. Suitable derivatives of rapamycin include e.g. compounds of formula I

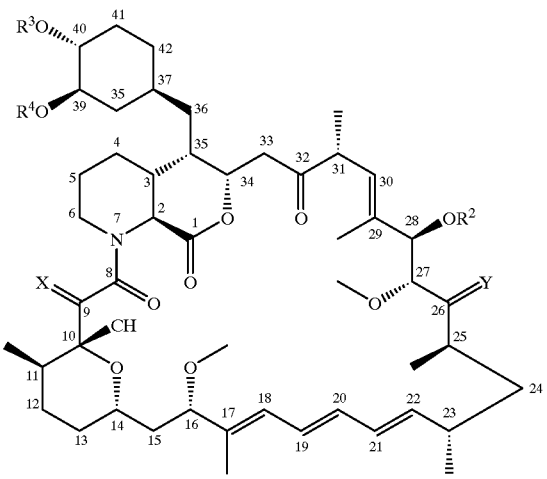

(I)

wherein

X is (H,H) or O;

Y is (H,OH) or O;

$R^1$ and $R^2$ are independently selected from

H,. alkyl, arylalkyl, hydroxyalkyl, dihydroxyalkyl, hydroxyalkoxycarbonylalkyl, hydroxyalkylarylalkyl, dihydroxyalkylarylalkyl, acyloxyalkyl, aminoalkyl, alkylaminoalkyl, alkoxycarbonylaminoalkyl, acylaminoalkyl, arylsulfonamidoalkyl, allyl, dihydroxyalkylallyl, dioxolanylallyl, dialkyl-dioxolanylalkyl, di(alkoxycarbonyl)-triazolyl-alkyl and hydroxy-alkoxy-alkyl; wherein "alk-" or "alkyl" is $C_{1-6}$alkyl, branched or linear; "aryl" is phenyl or tolyl; and acyl is a radical derived from a carboxylic acid; and $R^4$ is methyl or $R^4$ and $R^1$ together form $C_{2-6}$alkyl;

provided that $R^1$ and $R^2$ are not both H; and hydroxyalkoxy-alkyl is other than hydroxyalkoxymethyl.

Such compounds are disclosed in WO 94/09010 the contents of which, in particular with respect to the compounds, are incorporated herein by reference.

Acyl as may be present in $R_1$ or $R_2$, is preferably $R_aCO$— wherein $R_a$ is $C_{1-6}$alkyl, $C_{2-6}$alkenyl, $C_{3-6}$cycloalkyl, aryl, aryl $C_{1-6}$alkyl (wherein aryl is as defined above) or heteroaryl, e.g. a residue derived from a 5 or 6 membered heterocycle comprising N, S or O as a heteroatom and optionally one or two N as further heteroatoms. Suitable heteroaryl include e.g. pyridyl, morpholino, piperazinyl and imidazolyl.

Examples of such compounds include:

1. 40-O-Benzyl-rapamycin
2. 40-O-(4'-Hydroxymethyl)benzyl-rapamycin
3. 40-O-[4'-(1,2-Dihydroxyethyl)]benzyl-rapamycin
4. 40-O-Allyl-rapamycin
5. 40-O-[3'-(2,2-Dimethyl-1,3-dioxolan-4(S)-yl)-prop-2'-en-1'-yl]-rapamycin
6. (2'E,4'S)-40-O-(4',5'-Dihydroxypent-2'-en-1'-yl)-rapamycin
7. 40-O-(2-Hydroxy)ethoxycarbonylmethyl-rapamycin
8. 40-O-(2-Hydroxy)ethyl-rapamycin
9. 40-O-(3-Hydroxy)propyl-rapamycin
10. 40-O-(6-Hydroxy)hexyl-rapamycin
11. 40-O-[2-(2-Hydroxy)ethoxy]ethyl-rapamycin
12. 40-O-[(3S)-2,2-Dimethyldioxolan-3-yl]methyl-rapamycin
13. 40-O-[(2S)-2,3-Dihydroxyprop-1-yl]-rapamycin
14. 40-O-(2-Acetoxy)ethyl-rapamycin
15. 40-O-(2-Nicotinoyloxy)ethyl-rapamycin
16. 40-O-[2-(N-Morpholino)acetoxy]ethyl-rapamycin
17. 40-O-(2-N-Imidazolylacetoxy)ethyl-rapamycin
18. 40-O-[2-(N-Methyl-N'-piperazinyl)acetoxy]ethyl-rapamycin
19. 39-O-Desmethyl-39,40-O,O-ethylene-rapamycin
20. (26R)-26-Dihydro-40-O-(2-hydroxy)ethyl-rapamycin
21. 28-O-Methyl-rapamycin
22. 40-O-(2-Aminoethyl)-rapamycin
23. 40-O-(2-Acetaminoethyl)-rapamycin
24. 40-O-(2-Nicotinamidoethyl)-rapamycin
25. 40-O-(2-(N-Methyl-imidazo-2'-ylcarboxamido)ethyl)-rapamycin
26. 40-O-(2-Ethoxycarbonylaminoethyl)-rapamycin
27. 40-O-(2-Tolylsulfonamidoethyl)-rapamycin
28. 40-O-[2-(4',5'-Dicarboethoxy-1',2',3'-triazol-1'-yl)-ethyl]-rapamycin A preferred compound is e.g. 40-O-(2-hydroxy)ethyl-rapamycin (referred thereafter as Compound A).

Compounds of formula I have, on the basis of observed activity, e.g. binding to macrophilin-12 (also known as FK-506 binding protein or FKBP-12), e.g. as described in WO 94/09010, been found to be useful e.g. as immunosuppressants, e.g. in the treatment of acute allograft rejection.

Organ transplants of liver, kidney, lung and heart are now regularly performed as treatment for endstage organ disease. Because of the current shortage of human donors for transplantable allografts, attention has focused on the possibility of using xenografts (transplants between species) in transplantation. One of the major obstacles in transplanting successfully xenografts in humans is immunological.

A further obstacle in allo- and xenotransplantation is the chronic rejection and thus organ transplantation is not yet a clinically viable solution to irreversible organ disease.

Chronic rejection, which manifests as progressive and irreversible graft dysfunction, is the leading cause of organ transplant loss, in some cases already after the first postoperative year. The clinical problem of chronic rejection is clear from transplantation survival times; about half of kidney allografts are lost within 5 years after transplantation, and a similar value is observed in patients with heart allografts.

Chronic rejection is considered as a multifactorial process in which not only the immune reaction towards the graft but also the response of the blood vessel walls in the grafted organ to injury ("response-to-injury" reaction) plays a role.

The variant of chronic rejection with the worst prognosis is an arteriosclerosis-like alteration, also called transplant vasculopathy, graft vessel disease, graft arteriosclerosis, transplant coronary disease, etc. This vascular lesion is characterized by migration and proliferation of smooth muscle cells, probably under influence of growth factors that are amongst others synthesized by endothelial cells. This leads to intimal proliferation and thickening, smooth muscle cell hypertrophy repair, and finally to gradual luminal obliteration (vascular remodelling). It appears to progress also through repetitive endothelial injury induced amongst others by host antibody or antigen-antibody complexes; also so-called non-immunological factors like hypertension, hyperlipidemia, hypercholesterolemia etc. play a role.

Chronic rejection appears to be inexorable and uncontrollable because there is no known effective treatment or prevention modality. Thus, there continues to exist a need for a treatment effective in preventing, controlling or reversing manifestations of chronic graft vessel diseases.

There also continues to exist a need to prevent or treat restenosis or vascular occlusions as a consequence of proliferation and migration of intimal smooth muscle cell, e.g. induced by vascular surgeries such as angioplasty.

In accordance with the present invention, it has now surprisingly been found that compounds of formula I inhibit vasculopathies such as vascular remodelling and are particularly indicated to prevent or combat chronic rejection in a transplanted organ.

In accordance with the particular findings of the present invention, there is provided:
1. A method for preventing or treating neointimal proliferation and thickening in a subject in need thereof, comprising administering to said subject a therapeutically effective amount of a compound of formula I.

In a series of further specific or alternative embodiments, the present invention also provides:

2.1. A method for preventing or combating manifestations of chronic rejection in a recipient of organ or tissue transplant comprising the step of administering to said recipient a therapeutically effective amount of a compound of formula I.

2.2 A method for preventing or combating graft vessel diseases, e.g. transplant vasculopathies, arteriosclerosis or atherosclerosis, in a recipient of organ or tissue transplant, comprising the step of administering to said recipient a therapeutically effective amount of a compound of formula I.

By manifestations of chronic rejection are meant the conditions resulting from the immune reaction towards the graft and the response of the blood vessel walls in the grafted organ or tissue as indicated above. Compounds of formula I are useful for reducing chronic rejection manifestations or for ameliorating the conditions resulting from chronic rejection.

The organ or tissue transplantation may be performed from a donor to a recipient of a same or different species. Among such transplanted organs or tissues and given illustratively are heart, liver, kidney, spleen, lung, small bowel, and pancreas, or a combination of any of the foregoing.

In a further or alternative embodiment the invention provides:
3. A method for preventing or treating intimal smooth muscle cell proliferation and migration, e.g. restenosis, and/or vascular occlusion following vascular injury, e.g. angioplasty, in a subject in need thereof, comprising administering to said subject a therapeutically effective amount of a compound of formula I.

In a further or alternative embodiment, the present invention also provides:
4. A method for preventing or combating acute or chronic rejection in a recipient of organ or tissue xenograft transplant comprising administering to said recipient a therapeutically effective amount of a compound of formula I.

Xenograft organ or tissue transplants include e.g. heart, liver, kidney, spleen, lung, small bowel, pancreatic (complete or partial, e.g. Langerhans islets), skin and bone marrow xenografts.

As alternative to the above the present invention also provides:
5. A compound of formula I for use in any method as defined under 1 to 4 above; or
6. A compound of formula I for use in the preparation of a pharmaceutical composition for use in any method as defined under 1 to 4 above; or
7. A pharmaceutical composition for use in any method as defined under 1 to 4 above comprising a compound of formula I together with one or more pharmaceutically acceptable diluents or carriers therefor.

Utility of the compounds of formula I in treating diseases and conditions as hereinabove specified, may be demonstrated in animal tests, for example in accordance with the methods hereinafter described.

A. Chronic Allograft Rejection

The kidney of a male DA (RT1$^a$) rat is orthotopically transplanted into a male Lewis (RT1$^1$) recipient. In total 24 animals are transplanted. All animals are treated with cyclosporine A at 7.5 mg/kg/day per os for 14 days starting on the day of transplantation, to prevent acute cellular rejection. Contralateral nephrectomy is not performed. Each experimental group treated with a distinct dose of a compound of formula I or placebo comprises six animals.

Starting at day 53–64 after transplantation, the recipient animals are treated per os for another 69–72 days with a compound of formula I or receive placebo. At 14 days after transplantation animals are subjected to graft assessment by magnetic resonance imaging (MRI) with perfusion measurement of the kidneys (with comparison of the grafted kidney and the own contralateral kidney). This is repeated at days 53–64 after transplantation and at the end of the experiment. The animals are then autopsied. Rejection parameters such as MRI score, relative perfusion rate of the grafted kidney and histologic score of the kidney allograft for cellular rejection and vessel changes are determined and statistically analyzed. Administration of a compound of formula I, e.g. Compound A, at a dose of 0.5 to 2.5 mg/kg in this rat kidney allograft model yields a reduction in all above mentioned rejection parameters. In this assay, animals treated per os with 2.5 mg/kg/day of Compound A have a significantly lower MRI score of rejection, histologic score for cellular rejection and vessel changes and a significantly lower reduction in perfusion rate assessed by MRI than the animals of the placebo group.

B. Aorta Transplantation

In this model of aorta transplantation in the rat, an allogeneic response to the graft does not destroy the graft, but it evokes pathological changes resembling those of chronic rejection in clinical transplantation. These include infiltration into the adventitia of mononuclear cells (lymphocytes, macrophages, some plasma cells), and thickening of the intima.

Donor aorta between the branch of the renal artery and the start of the caudal mesenteric aorta, about 1 cm in length, is harvested from a male DA (RT1$^a$) rat and transplanted orthotopically in a male Lewis (RT1[1]) rat. Weekly after transplantation, the body weight is recorded. At autopsy, the graft with part of the aorta of the recipient just above and below the transplant is removed. It is perfused ex vivo with phosphate-buffered saline supplemented with 2% paraformaldehyde and 2.5% glutaraldehyde for about 2 minutes, then for 24 hours fixed by immersion fixation in the same solution, and thereafter fixed in 4% buffered formalin. Pieces of the graft are embedded in paraffin, in such a way that both a transversal section and a longitudinal section is made of the grafted aorta and the recipient's own aorta.

Sections of 4 $\mu$m thickness are stained by hematoxylin-eosin, elastica-von-Gieson and periodic-acid-Schiff. Apart from conventional light microscopy, images are recorded by confocal laser scanning microscopy. From each section, four areas are scanned, and from each area the thickness of the intima and intima+media is measured at five locations.

At autopsy, weight and histology is performed for thymus, spleen, liver, kidney, testes and seminal vesicles.

A first experiment includes 4 groups, each comprising 4 animals. In one group isogeneic transplantations (Lewis to Lewis) are performed, and animals receive a placebo microemulsion, the other groups comprise allogeneic transplantations, and animals receive per os either placebo microemulsion or a compound of formula I in microemulsion at 2.5 mg/kg/day. The experiment is terminated at 7 weeks after transplantation.

A second experiment includes 4 groups, each comprising 4 animals. In all cases allogeneic transplants are performed, and animals receive per os either placebo microemulsion or a compound of formula I in microemulsion at 0.63, 1.25, 2.5 or 5.0 mg/kg/day. The experiment is terminated 11 weeks after transplantation.

In both experiments, the compounds of formula I, particularly Compound A significantly inhibit graft infiltration and neointima formation.

C. Angioplasty

Studies on anioplasty are done in the model of balloon catheter injury: Balloon catheterization is performed on day 0, essentially as described by Powell et al. (1989). Under Isofluorane anaesthesia, a Fogarty 2F catheter is introduced into the left common carotid artery via the external carotid and inflated (distension$\approx$10 $\mu$l H2O). The inflated balloon is withdrawn along the length of the common carotid three times, the latter two times whilst twisting gently to obtain a uniform de-endothelialization. The cathether is then removed, a ligature placed around the external carotid to prevent bleeding and the animals allowed to recover.

2 groups of 12 RoRo rats (400 g, approximately 24 weeks old) are used for the study: one control group and one group receiving the compound of formula I. The rats are fully randomized during all handling, experimental procedures and analysis.

The compound to be tested is administered p.o. (gavage) starting 3 days before balloon injury (day −3) until the end of the study, 14 days after balloon injury (day +14). Rats are kept in individual cages and allowed food and water ad libidum.

The rats are then anaesthetized with Isofluorane, a perfusion catheter inserted through the left ventricle and secured in the aortic arch, and an aspiration cannula inserted into the right ventricle. Animals are perfused under a perfusion pressure of 150 mmHg, firstly for 1 min. with 0.1 M phosphate buffered saline solution (PBS, pH 7.4) and then for 15 min. with 2.5 % glutaraldehyde in phosphate buffer (pH 7.4). The perfusion pressure is 150 mmHg at the tip of the cannula ($\approx$100 mmHg in the carotid artery), as determined in a preliminary experiment by introducing a cannula attached to a pressure transducer into the external carotid). Carotid arteries are then excised, separated from surrounding tissue and immersed in 0.1 M cacodylate buffer (pH 7.4) containing 7% saccharose and incubated overnight at 4° C. The following day the carotids are immersed and shaken for 1 h at room temperature in 0.05% KMnO4 in 0.1 M cacodylate. The tissues are then dehydrated in a graded ethanol series; 2×10 min in 75%,2×10 min in 85%, 3×10 min in 95% and 3×10 min in 100% ethanol. The dehydrated carotids are then embedded in Technovit 7100 according to the manufacturers recommendation. The embedding medium is left to polymerize overnight in an exsiccator under argon, since oxygen is found to inhibit proper hardening of the blocks.

Sections 1–2 $\mu$m thick are cut from the middle section of each carotid with a hard metal knife on a rotary microtome and stained for 2 min with Giemsa stain. About 5 sections from each carotid are thus prepared and the cross-sectional area of the media, neointima and the lumen morphometrically evaluated by means of an image analysis system (MCID, Toronto, Canada).

In this assay, the compounds of formula I inhibit myointimal proliferation when administered per os at a daily dose of from 0.5 to 2.5 mg/kg. Intimal thickening is significantly less in the vessels of the rats that receive Compound A compared to the control animals, e.g. at 0.5 mg/kg statistical inhibition of neointima formation of 50%, at 2.5 mg/kg significant inhibition of 75%.

D. In vivo Heart Xenotransplantation (Hamster-to-rat)

The hamster-into-rat xenograft combination is a so-called difficult concordant combination. Rats do not have natural anti-hamster antibody in sufficient amounts to yield immediate hyperacute rejection as observed in concordant combinations; however, rejection in untreated recipients occurs within 3–4 days, by antibodies in combination with complement. This is visualized in histology by destruction of blood vessels, exsudation and extravasation of erythrocytes, and influx by polymorpho-nuclear granulocytes; often there are signs of hemorrhage and thrombosis. Once this rejection has been overcome by effective inhibition of antibody synthesis or complement inactivation, a cellular rejection can emerge later on. This is visualized in histology by influx of mono-nuclear cells, including lymphocytes, lymphoblastoid cells, and macrophages, and destruction of the myocyte parenchyma. The inhibition of cellular rejection requires more immuno-suppression than that of allografts. Congenitally athymic (rnu/rnu) rats lack a competent (thymus-dependent) cellular immune system and generally are unable to reject allografts. Such animals do reject a hamster xenograft within 3–4 days in a similar fashion as euthymic rats, indicative that (at least part of) anti-hamster antibody synthesis in rats occurs following a thymus-independent B-cell response. Such recipients are useful in hamster xenografting to evaluate rejection by thymus-independent antibody-mediated rejection.

The heart of a Syrian hamster is heterotopically transplanted in the abdomen of a male Lewis (RT1') rat with anastomoses between the donor and recipient's aorta and the donor right pulmonary artery to the recipient's inferior vena cava. The graft is monitored daily by palpation of the abdomen. Rejection is concluded in case of cessation of heart beat. Animals are weighed weekly. In the present series of experiments, the endpoint is set to 28 days. Animals are subjected to autopsy; apart from the graft, weight and histoloy is assessed for thymus, spleen, liver, seminal vesicles and testes. Blood is taken and processed to serum for the determination of cytolytic anti-hamster erythrocyte antibody and hemolytic complement activity.

In this assay, compounds of formula I, e.g. Compound A, result in prolonged graft survival, in both athymic and euthymic recipients.

Daily dosages required in practicing the method of the present invention will vary depending upon, for example, the compound of formula I employed, the host, the mode of administration and the severity of the condition to be treated. A preferred daily dosage range is about from 0.25 to 25 mg as a single dose or in divided doses.

Suitable daily dosages for patients are on the order of from e.g. 0.2 to 25 mg p.o. preferably 5 to 25. The compounds of formula I may be administered by any conventional route, in particular enterally, e.g. orally, e.g. in the form of tablets, capsules, drink solutions, nasally, pulmonary (by inhalation) or parenterally, e.g. in the form of injectable solutions or suspensions. Suitable unit dosage forms for oral administration comprise from ca. 0.05 to 12.5 mg, usually 1 to 10 mg active ingredient, e.g. Compound A, together with one or more pharmaceutically acceptable diluents or carriers therefor.

When used to prevent or treat chronic rejection or xenotransplant rejection as hereinabove specified the compounds of formula I may be administered as the sole active ingredient or together with other drugs in immunomodulating regimens. For example, the compounds of formula I may be used in combination with cyclosporins or ascomycins, or their immunosuppressive analogs, e.g. cyclosporin A, cyclosporin G, FK-506, etc.; cortieosteroids; cyclophosphamide; azathioprene; methotrexate; brequinar; leflunomide; mizoribine; mycophenolic acid; mycophenolate mofetil; 15-deoxyspergualine, immunosuppressive monoclonal antibodies, e.g., monoclonal antibodies to leukocyte receptors, e.g., MHC, CD2, CD3, CD4, CD7, CD25, CD28, B7, CD45, or CD58 or their ligands; or other immunomodulatory compounds, e.g. CTLA41 g.

Where the compounds of formula I are administered in conjunction with other immunosuppressive/ immunomodulatory, therapy, e.g. for preventing or treating chronic rejection or xenotransplant rejection as hereinabove specified, dosages of the co-administered immunosuppressant or immuno-modulatory compound will of course vary depending on the type of co-drug employed, e.g. whether it is a steroid or a cyclosporin, on the specific drug employed, on the condition being treated, and so forth. In accordance with the foregoing the present invention provides in a yet further aspect:

8. A method as defined above comprising co-administration, e.g. concomitantly or in sequence, of a therapeutically effective amount of a compound of formula I and a second drug substance, said second drug substance being an immunosuppressant or immunomodulatory drug, e.g. as indicated above.

FORMULATION EXAMPLE

Capsules

| Ethanol | 20.0 mg |
|---|---|
| 1,2-propylene glycol | 81.0 mg |
| Refined oil | 121.5 mg |
| Cremophor RH40 | 202.5 mg |
| Compound A | 20.0 mg |
| Total | 500 mg |

Compounds of formula I are well tolerated at dosages required for use in accordance with the present invention. For example, the NTEL for Compound A in a 4-week toxicity study is 0.5 mg/kg/day in rats and 1.5 mg/kg/day in monkeys.

What is claimed is:

1. A method for preventing or treating:

neointimal proliferation and thickening and/or restenosis and/or vascular occlusion following vascular injury comprising administering to a subject in need thereof an effective amount of 40-O-(2-hydroxy)ethyl-rapamycin.

2. A method according to claim 1 for preventing or treating neointimal proliferation and thickening.

3. A method according to claim 1 for preventing or treating restenosis and/or vascular occlusion following vascular injury.

4. A method according to claim 1 for preventing or treating vascular occlusion following vascular injury.

* * * * *

UNITED STATES PATENT AND TRADEMARK OFFICE
CERTIFICATE OF CORRECTION

PATENT NO. : 6,384,046 B1
DATED : May 7, 2002
INVENTOR(S) : Schuler et al.

It is certified that error appears in the above-identified patent and that said Letters Patent is hereby corrected as shown below:

<u>Title page,</u>
Item [54], should read: -- USE OF 40-O-(2-HYDROXY)ETHYLRAPAMYCIN FOR TREATMENT OF RESTENOSIS AND OTHER DISORDERS --.

Signed and Sealed this

Twenty-second Day of October, 2002

Attest:

Attesting Officer

JAMES E. ROGAN
*Director of the United States Patent and Trademark Office*